United States Patent
Tano et al.

(10) Patent No.: US 9,283,356 B2
(45) Date of Patent: Mar. 15, 2016

(54) GUIDE WIRE

(71) Applicant: TERUMO KABUSHIKI KAISHA, Shibuya-ku (JP)

(72) Inventors: Yutaka Tano, Fujinomiya (JP); Yousuke Nabeshima, Fujinomiya (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 5 days.

(21) Appl. No.: 14/339,101

(22) Filed: Jul. 23, 2014

(65) Prior Publication Data

US 2014/0336622 A1 Nov. 13, 2014

Related U.S. Application Data

(63) Continuation of application No. PCT/JP2013/051271, filed on Jan. 23, 2013.

(30) Foreign Application Priority Data

Jan. 30, 2012 (JP) .................................. 2012-016800

(51) Int. Cl.
*A61M 25/00* (2006.01)
*A61M 25/09* (2006.01)
*B23K 26/20* (2014.01)

(52) U.S. Cl.
CPC ................ *A61M 25/09* (2013.01); *B23K 26/20* (2013.01); *A61M 2025/006* (2013.01); *A61M 2025/0062* (2013.01); *A61M 2025/0915* (2013.01); *A61M 2025/09066* (2013.01); *A61M 2025/09108* (2013.01); *A61M 2025/09133* (2013.01)

(58) Field of Classification Search
CPC ................................ A61M 25/09; B23K 23/20

USPC ......................................................... 600/585
See application file for complete search history.

(56) References Cited

U.S. PATENT DOCUMENTS 7,753,859 B2 7/2010 Kinoshita et al.
2007/0255217 A1 11/2007 Burkett et al.
(Continued)

FOREIGN PATENT DOCUMENTS

| JP | 49-52404 | 5/1974 |
| JP | 2008-307367 A | 12/2008 |
| WO | WO 2010/018762 A1 | 2/2010 |
| WO | WO 2011/118443 A1 | 9/2011 |

OTHER PUBLICATIONS

International Search Report (PCT/ISA/210) mailed on Feb. 19, 2013, by the Japanese Patent Office as the International Searching Authority for International Application No. PCT/JP2013/051271.
(Continued)

*Primary Examiner* — Brian Szmal
(74) *Attorney, Agent, or Firm* — Buchanan Ingersoll & Rooney PC (57) ABSTRACT

A guide wire includes an elongated wire body exhibiting flexibility, a distal side coating layer that covers a distal portion of the wire body and is made of a resin material, and a tubular member through which the wire body passes and possessing a distal portion positioned in the vicinity of a proximal portion of the distal side coating layer. A plurality of melted portions which are concavely deformed toward the wire body side by melting are formed in the tubular member. The tubular member is fixed to the wire body by bringing the melted portions into press-contact with the wire body The plurality of melted portions is irregularly formed along an axis direction of the tubular member.

18 Claims, 5 Drawing Sheets

(56) References Cited

U.S. PATENT DOCUMENTS

2008/0281230 A1 11/2008 Kinoshita et al.
2013/0006222 A1 1/2013 Nabeshima et al.

OTHER PUBLICATIONS

The extended European search report issued on Jul. 13, 2015, by the European Patent Office in corresponding European Patent Application No. 13744028.5-1506. (8 pages).

GUIDE WIRE

CROSS REFERENCES TO RELATED APPLICATIONS

This application is a continuation of International Application No. PCT/JP2013/051271 filed on Jan. 23, 2013, and claims priority to Japanese Application No. 2012-016800 filed on Jan. 30, 2012, the entire content of both of which is incorporated herein by reference.

TECHNICAL FIELD

The present invention generally relates to a guide wire.

BACKGROUND DISCUSSION

When inserting a catheter into a living body lumen such as a digestive tract and a blood vessel, a guide wire is employed to guide the catheter to a target site of the living body lumen. The guide wire is employed by being inserted into the inside of the catheter. In addition, observation or treatment for the living body lumen is performed by employing an endoscope, and thus, the guide wire is also employed to guide the catheter inserted into the endoscope or a lumen of the endoscope to the target site of the living body lumen.

A guide wire is known which has an elongated wire body, a resin coating layer covering a distal portion of the wire body and an annular member arranged on a proximal side of the resin coating layer. Examples of such a guide wire are disclosed Japanese Application Publication No. 2008-307367 and International Application Publication No, 2011/118443. The guide wire disclosed in these application publications prevents curling of the resin coating layer by defining a proximal outer diameter of the resin coating layer and a distal outer diameter of the annular member. But guide wires which can further prevent such curling are desired.

SUMMARY

According to one aspect, a guide wire comprises a flexible elongated wire body, a distal side coating layer covering a distal portion of the wire body and comprised of a resin material, and a tubular member mounted on the wire body and possessing a distal portion positioned in a vicinity of a proximal portion of the distal side coating layer. The tubular member includes a plurality of melted portions concavely deformed toward the wire body by melting, and the tubular member is fixed to the wire body by virtue of the melted portions being in press-contact with the wire body.

The melted portions can be irregularly or non-symmetrically formed along the axial direction of the tubular member.

The sites of the tubular member corresponding to the melted portions possess a rigidity lower than that of other sites of the tubular member.

The melted portions are formed in a proximal portion of the tubular member.

The tubular member has a tapered portion of which the outer diameter is tapered toward the proximal side, and the melted portions are formed in the tapered portion.

According to another aspect, a guide wire comprises: a flexible elongated wire body possessing a distal end portion and a proximal end portion, a resin coating layer covering the distal end portion of the wire body, and a tubular member mounted on the wire body so that the wire body passes though the tubular member while the tubular member encircles the wire body. The tubular member possesses a distal end in direct contact with the proximal end of the resin coating layer, and at least the proximal end portion of the tubular member encircles a portion of the wire body that is devoid of the resin coating layer. The tubular member includes a plurality of circumferentially spaced apart melted portions at each of which the outer surface of the tubular member is concavely recessed and the inner surface of the tubular member projects as a protrusion in direct contact with the outer surface of the wire body to positionally fix the tubular member relative to the wire body. In addition, the inner surface of the tubular member at places other than the protrusions is spaced from the outer surface of the wire body.

Another aspect disclosed here involves method of fabricating a guide wire. The method includes positioning a tubular member in surrounding relation to an elongated wire, with the wire including a distal portion covered by a resin coating layer. The tubular member is positioned in surrounding relation to the elongated wire such that the tubular member directly contacts the proximal end of the resin coating layer. The method further comprises laser irradiating the tubular member at a plurality of spaced apart locations to melt material forming the tubular member and produce a plurality of spaced apart melted portions at each of which the outer surface of the tubular member is concavely recessed and the inner surface of the tubular member projects as a protrusion in direct contact with the outer surface of the wire body to positionally fix the tubular member relative to the wire body.

According to the guide wire and method disclosed here, the tubular member and the wire (wire body) are firmly fixed to each other by the melted portions of the tubular member. Even if the wire is curved near the tubular member, the tubular member curves along the wire. Therefore, since relatively smooth bending can be realized without forming an unnecessary gap between the tubular member and the wire body, it is possible to prevent a proximal side of a distal side coating layer from being curled.

DETAILED DESCRIPTION

Firstly, a guide wire according to a first embodiment will be described with reference to FIGS. 1, 2 and 3. In the description which follows, for convenience of description, the right side in FIG. 1 (similarly applied to FIGS. 2 and 3 which will be described below) is referred to as a "proximal" side, and the left side is referred to as a "distal" side. In addition, in each drawing, in order to facilitate understanding, the guide wire is schematically illustrated in such a manner that the guide wire is shortened in a longitudinal direction and is extended in the thickness direction, respectively. A ratio of dimensions in the longitudinal direction to dimensions in the thickness direction is thus different from the actual ratio.

Figure 1:
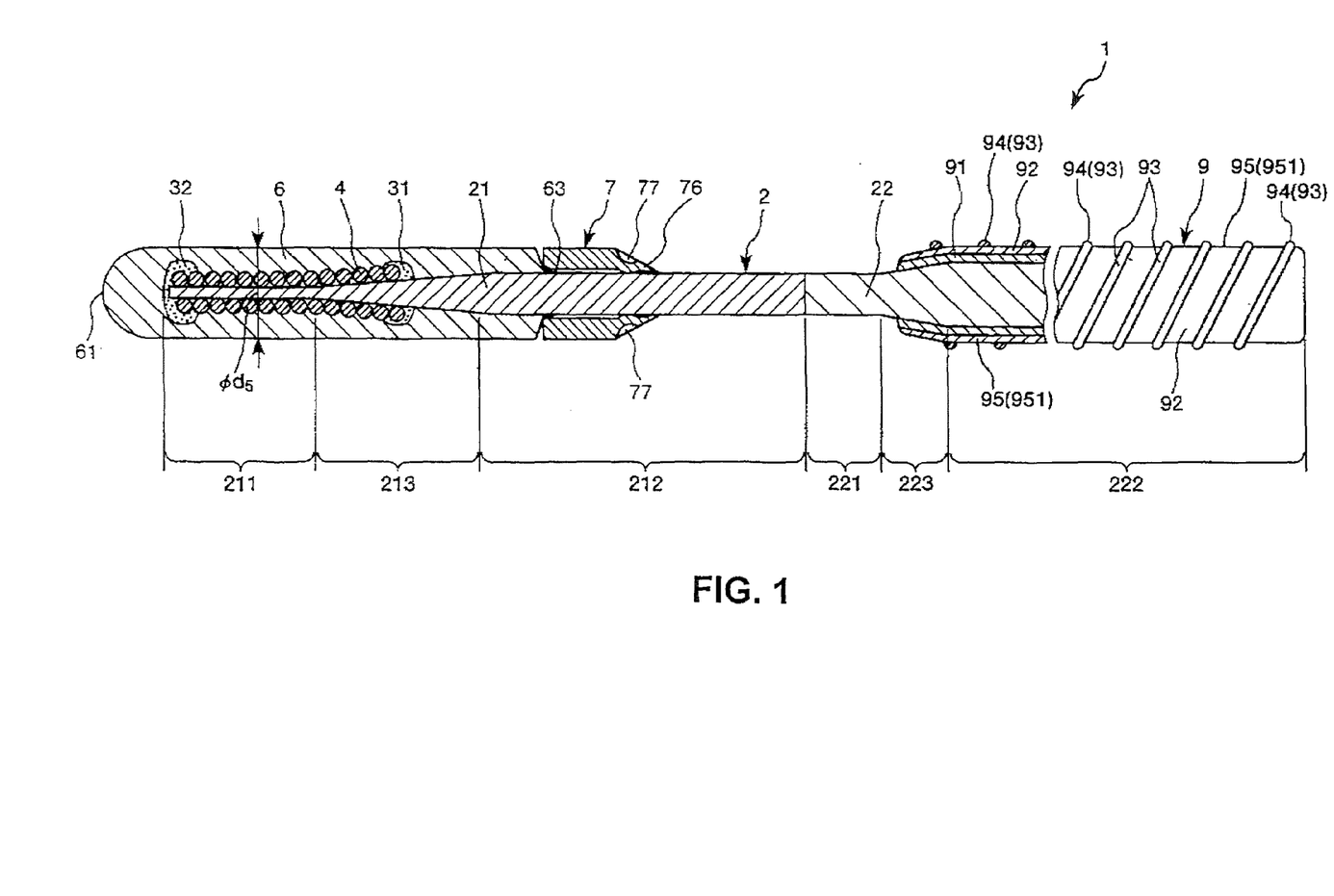
FIG. 1 is a vertical cross-sectional view of a first embodiment of a guide wire representing an example of the guide wire disclosed here.
Figure 2:
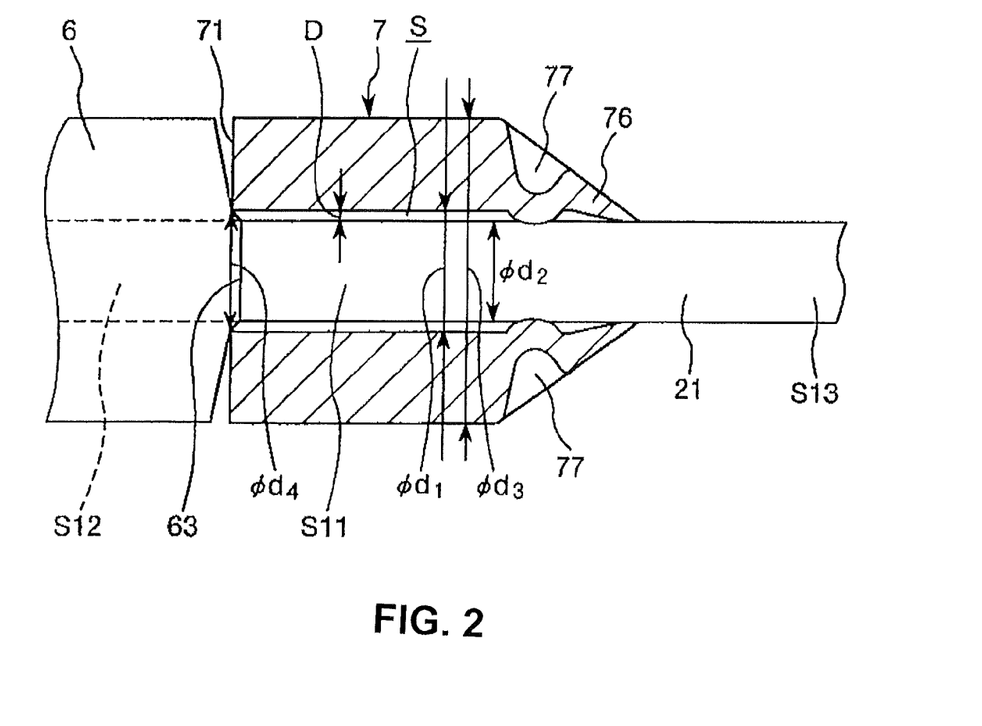
FIG. 2 is an enlarged cross-sectional view of a tubular member included in the guide wire illustrated in FIG. 1.

The guide wire 1 illustrated in FIGS. 1 and 2 is a catheter guide wire which is inserted in the lumen of a catheter (also including an endoscope) to be employed. The guide wire 1 includes an elongated wire body 2, a spiral coil 4, a distal side coating layer 6 (hereinafter referred to as "resin coating layer 6"), and a tubular member 7 protruding outwardly from the wire body 2.

An overall length of the guide wire 1 is not particularly limited, but it is preferable that the overall length be approximately 200 mm to 5,000 mm. In addition, the average outer diameter of the guide wire 1 is not particularly limited, but it is preferable that the average outer diameter be approximately 0.2 mm to 1.2 mm.

As illustrated in FIG. 1, the wire body 2 is comprised of a first wire 21 arranged on the distal side of the wire body and a second wire 22 arranged on the proximal side of the first wire 21. The first wire 21 and the second wire 22 are firmly connected or fixed to each other by welding.

A method of welding the first wire 21 and the second wire 22 is not particularly limited. Examples of the welding method which can be employed include spot welding employing a laser, butt resistance welding such as butt seam welding, and the like. However, it is preferable to use the butt resistance welding.

The first wire 21 is a wire having elasticity. The length of the first wire 21 is not particularly limited, but it is preferable that the length be approximately 20 mm to 1,000 mm.

In the present embodiment, the first wire 21 is comprised of two constant outer diameter portions 211 and 212 positioned at both end portions of the first wire 21, and another portion 213 (tapered portion) which does not possess a constant outer diameter. The two constant outer diameter portions 211 and 212 are axially spaced apart from one another by the portion 213 that does not possess a constant outer diameter. The other portion 213 is thus positioned between the two constant outer diameter portions 211 and 212. The outer diameter of the constant outer diameter portion 211 is constant throughout its longitudinal extent, and the outer diameter of the constant outer diameter portion 212 is constant throughout its longitudinal extent. The outer diameters of the two constant outer diameter portions 211 and 212 differ from one another, with the outer diameter of the constant outer diameter portion 211 being less than the outer diameter of the constant outer diameter portion 212. The tapered portion (first gradually decreasing outer diameter portion) 213, which is positioned between the two constant outer diameter portions 211 and 212, possesses an outer diameter that gradually decreases toward the distal direction.

By disposing the tapered portion 213 between the two constant outer diameter portions 211 and 212, it is possible to gradually decrease the rigidity (flexural rigidity, torsional rigidity) of the first wire 21 toward the distal direction. As a result, the guide wire 1 exhibits rather excellent softness in the distal portion, thereby improving a blood vessel tracking property and safety while also preventing the guide wire 1 from being bent.

The length of the tapered portion 213 is not particularly limited, but it is preferable that the length is approximately 10 mm to 1,000 mm, and it is more preferable that the length is approximately 20 mm to 300 mm. If the length is within this range, it is possible to more gradually change the rigidity along the longitudinal direction or longitudinal extent of the tapered portion.

In the present embodiment, the tapered portion 213 has a tapered shape of which the outer diameter continuously decreases toward the distal direction at a substantially constant decreasing rate. In other words, the tapering angle of the tapered portion 213 is substantially constant along the longitudinal direction or longitudinal extent of the tapered portion 213. Accordingly, the guide wire 1 can be gradually changed in rigidity along the longitudinal direction.

It is also possible, as an alternative, to configure the tapered portion so that the tapering angle of the tapered portion 213 changes along the longitudinal direction or longitudinal extent of the tapered portion. For example, the tapered portion 213 may be formed by alternately repeating relatively large tapering angle portions and relatively small tapering angle portions multiple times. In this case, the tapered portion 213 may have a portion of which the tapering angle is zero degrees.

It is preferable that the material forming the first wire 21 be a metal material. For example, it is possible to use various metal materials such as stainless steel (for example, SUS304, SUS303, SUS316, SUS316L, SUS316J1, SUS316J1L, SUS405, SUS430, SUS434, SUS444, SUS429, SUS430F, SUS302, and the like) and pseudo-elastic alloys (including super-elastic alloy). However, it is preferable to use a super-elastic alloy. Since the super-elastic alloy is relatively soft, is resilient, and is unlikely to be bent, the first wire 21 is configured with the super-elastic alloy, and thus, the guide wire 1 possesses sufficient softness and resilience with respect to bending in a distal side portion of the first wire 21. Moreover, the property of tracking blood vessels, which are complicatedly curved and bent, is improved, and more excellent operability can be obtained. When the first wire 21 is made of a super-elastic alloy, the first wire is able to undergo repeated bending and curving while resisting permanent deformation. Therefore, it is possible to prevent a degraded operability which is caused by a bending tendency of the first wire 21 while using the guide wire 1.

The pseudo-elastic alloy includes those which have any shape of stress-strain curves caused by tension, those which can significantly measure a transformation point such as As, Af, Ms, and Mf, those which cannot measure the transformation point, and all of those which are largely deformed by stress and are substantially restored to their original shapes by eliminating the stress.

Examples of a preferable composition of the super-elastic alloy include Ni—Ti-based alloys such as Ni—Ti alloys containing Ni in a range of 49 at % to 52 at %, Cu—Zn alloys containing Zn in a range of 38.5 wt % to 41.5 wt %, Cu—Zn—X alloys containing X in a range of 1 wt % to 10 wt % (X is at least one type among Be, Si, Sn, Al and Ga), and Ni—Al alloys containing Al in a range of 36 at % to 38 at %. Among these, a particularly preferable composition is the aforesaid Ni—Ti-based alloys.

The distal portion (distal-most end) of the second wire 22 is interlocked with or fixed to the proximal portion (proximal-most end) of the first wire 21. The second wire 22 is a wire having elasticity. The length of the second wire 22 is not particularly limited, but it is preferable that the length be approximately 20 mm to 4,800 mm.

In the present embodiment, the second wire 22 is comprised of two constant outer diameter portions 221 and 222 positioned at both end portions of the second wire 22, and another portion 223 (tapered portion) which does not possess a constant outer diameter. The two constant outer diameter portions 221 and 222 are axially spaced apart from one another by the portion 223 that does not possess a constant outer diameter. The other portion 223 is thus positioned between the two constant outer diameter portions 221 and 222. The outer diameter of the constant outer diameter portion 221 is constant throughout its longitudinal extent, and the outer diameter of the constant outer diameter portion 222 is constant throughout its longitudinal extent. The outer diameters of the two constant outer diameter portions 221 and 222 differ from one another, with the outer diameter of the constant outer diameter portion 221 being less than the outer diameter of the constant outer diameter portion 222. The outer diameter of the constant outer diameter portion 221 of the second wire is substantially equal to the outer diameter of the constant outer diameter portion 212 of the first wire 21.

By disposing the tapered portion 223 in the second wire 22, it is possible to gradually decrease rigidity of the second wire 22 (flexural rigidity, torsional rigidity) toward the distal direction. As a result, the operability and safety are improved when the guide wire 1 is inserted into a living body.

In the present embodiment, the tapered portion 223 has a tapered shape of which the outer diameter continuously decreases toward the distal direction at a substantially constant decreasing rate. In other words, the tapering angle of the tapered portion 223 is substantially constant along the longitudinal direction or longitudinal extent of the tapered portion 223. Accordingly, the guide wire 1 can be gradually changed in rigidity along the longitudinal direction or longitudinal extent.

It is also possible as an alternative that the tapering angle of the tapered portion 223 may be changed along the longitudinal direction. For example, the tapered portion 223 may be formed by alternately repeating relatively large tapering angle portions and relatively small tapering angle portions multiple times. In this case, the tapered portion 223 may have a portion of which the tapering angle is zero degrees.

It is preferable that a material (element) used to make the second wire 22 be metal material. It is possible to use various metal materials such as the stainless steel (for example, all types of SUS such as SUS304, SUS303, SUS316, SUS316L, SUS316J1, SUS316J1L, SUS405, SUS430, SUS434, SUS444, SUS429, SUS430F, SUS302, and the like), a piano wire, a cobalt-based alloy, and the pseudo-elastic alloy.

Among these, the cobalt-based alloy has a high elastic modulus when formed into a wire, and an appropriate elastic limit. Therefore, the second wire 22 configured with the cobalt-based alloy has particularly excellent torque transmissibility, and thus, a problem of buckling is extremely unlikely to occur. As long as the cobalt-based alloy contains Co as a constituent element, any one may be employed. However, it is preferable to use those which contain Co as a main component (Co-based alloy: among constituent elements of the alloy, an alloy of which Co content rate is the highest in a weight ratio). It is more preferable to employ Co—Ni—Cr-based alloys. The alloy with such a composition has plasticity for deformation at room temperature. Accordingly, for example, it is possible to relatively easily change the alloy into a desired shape when in use. In addition, the alloy with such a composition has a relatively high elastic coefficient and can be subjected to cold forming with the high elastic limit. Since the alloy has the high elastic limit, it is possible to reduce the diameter while sufficiently preventing occurrence of the buckling. Therefore, it is possible for the second wire 22 to be provided with the sufficient softness and the rigidity to be inserted in a predetermined site.

In addition, when the stainless steel is employed as the configuring material of the second wire 22, the guide wire 1 can acquire more excellent thrust-in performance and the torque transmissibility.

In the guide wire 1, the first wire 21 and the second wire 22 are configured with or made of the same type of alloy. The alloy is preferably a pseudo-elastic alloy, and Ni—Ti-based alloy is an example.

In the guide wire 1, the first wire 21 and the second wire 22 may be configured with different types of alloys. In this case, it is preferable that the first wire 21 be configured with a material having an elastic modulus lower than the elastic modulus of the material forming the second wire 22. This allows the guide wire 1 to have the excellent softness in the distal side portion while also exhibiting sufficient rigidity (flexural rigidity, torsional rigidity) in the proximal side portion. As a result, the guide wire 1 acquires the excellent thrust-in performance and the torque transmissibility. While ensuring good operability, the guide wire 1 exhibits good softness and the resilience on the distal side. In this regard, the blood vessel tracking property and the safety are improved.

In addition, as a specific combination between the first wire 21 and the second wire 22, it is preferable that the first wire 21 be configured with the super-elastic alloy (Ni—Ti alloy) and the second wire 22 be configured with the stainless steel. This allows the aforementioned effects to be more conspicuous.

The coil 4 is arranged to extend around the outer periphery of the distal portion of the wire body 2. The coil 4 is a member formed by winding a wire element in a spiral shape and covers the outer periphery of the distal portion of the wire body 2. The wire body 2 is inserted through or positioned inside a substantially central portion of the coil 4. In addition, in the guide wire 1, the coil 4 is in contact with the wire body 2, that is, the inner peripheral surface of the coil 4 is in close contact with the outer peripheral surface of the wire body 2. However, without being limited thereto, for example, the coil 4 may also be separated from the outer peripheral surface of the wire body 2.

In addition, in the guide wire 1, in a state in which an external force is not applied to the coil, the coil 4 has no gap between the axially adjacent helical or spiral windings of the coil 4. As an alternative, it is also possible to employ a configuration in which when an external force is not applied, a gap exist between the axially adjacent helical or spiral windings of the coil 4.

It is preferable that the coil 4 be made of an X-ray impermeable metal material (material having X-ray contrast property). Examples of such material include precious metals such as gold, platinum, tungsten, or alloys containing these (for example, platinum-iridium alloy) can be exemplified. Since the coil 4 is configured with the X-ray impermeable metal material, the guide wire 1 can acquire the X-ray contrast property. Therefore, it is preferably possible to insert the guide wire 1 in the living body while checking a position of the distal portion in X-ray fluoroscopy.

A proximal portion of the coil 4 is fixed to the tapered portion 213 of the wire body 2 by a fixing material 31, and a distal portion of the coil 4 is fixed to the constant outer diameter portion 211 of the wire body 2 by a fixing material 32. The fixing materials 31 and 32 are respectively, for example, adhesive agents, but may also be solder (brazing material).

In addition, the guide wire 1 has a resin coating layer 6 which collectively covers the distal portion of the wire body 2, the entirety of the coil 4 and the entirety of the fixing materials 31 and 32. The resin coating layer 6 is in close contact with the outer periphery of the distal portion of the wire body 2. In the present embodiment, the resin coating layer 6 is not present inside the coil 4, but may be present inside the coil 4.

The resin coating layer 6 can be provided for various purposes. As an example, it is possible to provide the resin coating layer 6 to improve the operability of the guide wire 1 by enhancing a sliding property and to improve the safety when inserting the guide wire 1 in the blood vessels, and the like.

The resin coating layer 6 is made of a sufficiently soft material (soft material, elastic material). Without being particularly limited, examples of the material forming the resin coating layer 6 include a polyolefin such as a polyethylene and a polypropylene, a polyvinyl chloride, a polyester (PET, PBT, and the like), a polyamide, a polyimide, a polyurethane, a polystyrene, a polycarbonate, a silicone resin, a fluorine resin (PTFE, ETFE, PFA, and the like), composite materials thereof, various rubber materials such as a latex rubber and a silicone rubber, and composite materials obtained by combining two or more out of these materials. Of these materials, a urethane-based resin is particularly preferable. If the resin coating layer 6 is mainly made of a urethane-based resin, the softness in the distal portion of the guide wire 1 is further improved. Therefore, when inserting the guide wire 1 in the blood vessels and the like, it is possible to reliably prevent damage to an endothelial wall of the blood vessels and the like, thereby extremely enhancing the safety.

In addition, the distal surface 61 (distal-most end portion) of the resin coating layer 6 is rounded. Accordingly, it is possible to prevent damage to an endothelial wall of a body cavity such as blood vessels due to the distal surface 61. In addition, a proximal end 63 (proximal-most end) of the resin coating layer 6 is positioned in the constant outer diameter portion 212 of the wire body 2 (first wire 21).

In the resin coating layer 6, particles (filler) composed of the X-ray impermeable material may be dispersed. In this case, the guide wire 1 can acquire the X-ray contrast property. Therefore, it is possible to insert the guide wire 1 in the living body while checking the position of the distal portion under X-ray fluoroscopy. The X-ray impermeable material is not particularly limited, but examples include precious metals such as platinum, tungsten, or alloy materials containing these materials.

The thickness of the resin coating layer 6 is not particularly limited, but may be appropriately selected in view of a forming purpose, a configuring material and a forming method of the resin coating layer 6. In general, it is preferable that the average thickness of the resin coating layer 6 be approximately 5 µm to 500 µm, and it is more preferable that it be approximately 10 µm to 350 µm. The resin coating layer 6 may be a laminated body having two or more layers.

The coating layer 9 is formed to cover the proximal portion of the wire body 2, specifically, substantially the entire region from the proximal portion of the second wire to the tapered portion 223. The coating layer 9 is configured so that an inner layer 91, an outer layer 92 and a linear body 93 are formed (laminated) on the outer periphery of the wire body 2 in this order.

The inner layer 91 is formed on the outer periphery of the wire body 2. That is, the inner layer 91 directly contacts the outer periphery of the wire body 2. The resin material forming the inner layer 91 is not particularly limited, but is preferably a fluorine-based resin material, for example. In addition, the inner layer 91 contains two types of fluorine-based resin materials with compositions different from each other. For example, as two types of the fluorine-based resin material, it is possible to use polytetrafluoroethylene (PTFE) for one type and fluoride ethylene propylene (FEP) for the other type.

Furthermore, since the layer of the inner layer 91 is formed on the outer periphery of the wire body 2, for example, in order to improve adhesion to the wire body 2, the material forming the inner layer 91 contains a resin material functioning as a binder. The resin material is not particularly limited, but for example, a polysulfone, a polyimide, a polyether ether ketone, a polyarylene ketone, a polyphenylene sulfide, a polyarylene sulfide, a polyamide-imide, a polyether-imide, a polyimide sulfone, a polyarylsulfone, a polyarylether sulfone, a polyester, a polyether sulfone, and the like are examples of resin materials that can be used.

The thickness of the inner layer 91 is not particularly limited. But as an example, it is preferable that the thickness be 0.001 mm to 0.020 mm, more preferably 0.001 mm to 0.010 mm.

The outer layer 92 is formed on the inner layer 91. That is, the outer layer 92 directly contacts the outer periphery of the inner layer 91. The resin material forming the outer layer 92 is not particularly limited. By way of example, it is preferable to employ the fluorine-based resin material similar to that of the inner layer 91. As examples of the fluorine-based resin material, it is possible to employ polytetrafluoroethylene (PTFE), fluoride ethylene propylene (FEP), and the like.

The thickness of the outer layer 92 is not particularly limited. But as an example, it is preferable that the thickness be 0.001 mm to 0.030 mm, more preferably 0.001 mm to 0.015 mm.

The linear body 93 is formed on the outer layer 92. That is, the linear body 93 directly contacts the outer periphery of the outer layer 92. The linear body 93 is wound in a spiral or helical shape around the outer layer 92 as shown in FIG. 1. In this manner, the linear body 93 is provided around substantially the entire periphery of the second wire 22. In addition, the linear body 93 is coarsely wound so that the axially adjacent wires (axially adjacent windings of the linear body 93) are axially separated from each other. In the present embodiment, the number of the formed linear bodies 93 is one or more. When there are multiple formed linear bodies 93, the winding direction of the spiral forming each linear body 93 may be the same as each other or may be opposite to each other.

This linear body 93 imparts to the second wire 22 (wire body 2) a plurality of axially spaced apart convex portions or outwardly protruding portions 94 and a concave portion 95 formed between the axially adjacent convex portions 94 (linear bodies 93).

The resin material forming the linear body 93 is not particularly limited. By way of example, it is preferable to employ the fluorine-based resin material similar to that of the inner layer 91. As the fluorine-based resin material, for example, it is possible to employ the polytetrafluoroethylene (PTFE), the fluoride ethylene propylene (FEP), and the like.

In the guide wire 1, a frictional coefficient in the convex portion 94 (linear body 93) is less than the frictional coefficient in a bottom portion 951 (exposed portion of outer layer 92) of the concave portion 95.

The tubular member 7 is configured as a cylindrical (ring-shaped or annular) member and is fixed in place at the constant outer diameter portion 212 of the wire body 2 (first wire 21). The tubular member 7 protrudes outwardly from the wire body 2 away from the outer periphery of the wire body 2. The tubular member is mounted on the wire body at a position such that at least the proximal portion of the tubular member encircles a portion of the wire body that is devoid of the resin coating layer 6.

The inner diameter φd1 of the tubular member 7 is slightly greater than the outer diameter φd2 of the constant outer diameter portion 212 of the wire body 2. In other words, the relationship φd1>φd2 is satisfied, and a gap S is formed between the inner peripheral surface of the tubular member 7 and the outer peripheral surface of the constant outer diameter portion 212. The dimension (thickness) D of the gap S is not particularly limited, but it is preferable that the thickness D be approximately 5 µm to 30 µm. By forming the thickness D of the gap S as described above, the smaller the gap S is, the first wire 21 (wire body 2) can be moved in an integrated manner with the tubular member 7, thereby improving the operability. In addition, the tubular member 7 is movable with respect to the wire body 2 in a state of not being welded. That is, before the tubular body 7 is fixed relative to the wire body 2, the tubular body 7 is movable relative to or along the wire body 2. Accordingly, it is possible to simply manufacture the guide wire 1 through a manufacturing method described below.

In addition, a distal end 71 of the tubular member 7 contacts the resin coating layer 6, and the proximal end portion 63 of the resin coating layer 6 is positioned in the inner side or interior (gap S) of the tubular member 7. In other words, the distal end 71 of the tubular member 7 is positioned closer to the distal side than the proximal 63 of the resin coating layer 6. Stated differently, the axially facing distal end face of the tubular member 7 is located distally beyond the proximal-most end of the resin coating layer 6. Therefore, the proximal end 63 (proximal-most end) of the resin coating layer 6 is not exposed on a surface of the guide wire 1 (does not face outward from guide wire 1).

In addition, the outer diameter (maximum outer diameter) φd3 of the tubular member 7 is greater than the outer diameter φd4 of the resin coating layer 6 where the distal 71 of the tubular member 7 is positioned. This tubular member 7 causes the proximal end 63 of the resin coating layer 6 to be positioned further inside than an outer peripheral surface of the tubular member 7. That is, the part of the proximal end of the resin coating layer 6 creeps into the space S.

In addition, the outer diameter φd3 of the tubular member 7 is smaller than (or the same as) the maximum outer diameter φd5 of the resin coating layer 6 (see FIG. 1). The length of the tubular member 7 is also shorter than the length of the resin coating layer 6. Since there is the above described relationship of small and large sizes, for example, when the guide wire 1 moves inside the living body lumen, the resin coating layer 6 having a relatively high sliding property in the distal portion of the resin coating layer 6 abuts on the wall portion defining the living body lumen, in preference over the tubular member 7. That is, the resin coating layer 6 contacts the living body lumen, but the tubular member 7 does not contact the living body lumen because the outer diameter φd3 of the tubular member 7 is smaller than (or the same as) the maximum outer diameter φd5 of the resin coating layer 6. This enables the guide wire 1 to be operated without degrading the operability.

The length of the tubular member 7 is not particularly limited, but it is preferable that the length be approximately 0.5 mm to 2 mm. By virtue of this length, the tubular member 7 can have a length sufficient for exhibiting its function and can effectively prevent degradation in the operability of the guide wire 1 which is caused by an excessively lengthened tubular member 7.

Specifically, a section S11 where the tubular member 7 of the wire body 2 is provided has a rigidity higher than the rigidity of a section S12 on the distal side of the section S11 and a section S13 on the proximal side of the section S11. The section S11 is thus unlikely to be curved and deformed in comparison to the sections S12 and S13. If the section S11 which is unlikely to be curved is excessively long, there is a possibility that the operability (particularly, tracking property) of the guide wire 1 may be degraded. Therefore, by arranging the tubular member 7 to have the above-described length and shortening as much as possible the section S11 which is unlikely to be curved and deformed, it is possible to effectively prevent the above-described degradation in the operability.

A proximal portion of the tubular member 7 is a tapered portion 76 possessing an outer diameter gradually decreasing toward the proximal direction. Then, at the tapered portion 76, the tubular member 7 is fixed (bonded) to the wire body 2. By virtue of the tapered portion 76, it is possible to gradually change the rigidity (flexural rigidity, torsional rigidity) of the wire body 2 including the tubular member 7 toward the proximal direction. In addition, it is possible to further minimize a difference in rigidity between the distal side and the proximal side of the wire body which are divided at the boundary of the proximal end of the tubular member 7. As a result, it is possible to improve the blood vessel tracking property of the guide wire 1, and it is also possible to prevent the guide wire 1 from being bent.

In addition, the tapered portion 76 also functions as a step filling portion which fills a step between the wire body 2 and the tubular member 7. Therefore, a distal end of the catheter is guided to the tubular member 7 along the outer peripheral surface (sliding on the outer peripheral surface) of the tapered portion 76. In this manner, the step between the wire body 2 and the tubular member 7 is filled by the tapered portion 76, and thus, it is possible to prevent the catheter from being caught.

In the tapered portion 76, a plurality of melted portions 77 concavely deformed toward the wire body 2 by melting is formed. Each melted portion 77 includes the concave portion exposed to the exterior of the tubular body, and the convex portion (protrusion) projecting towards the outer surface of the wire body 2. Each melted portion 77 is in pressing (direct) contact with the wire body 2, and thus the tubular member 7 is fixed relative to the wire body 2. The tubular member 7 is thus provided with the plurality of circumferentially spaced apart melted portions 77 at each of which the outer surface of the tubular member 7 is concavely recessed and the inner surface of the tubular member 7 projects as a protrusion in direct contact with the outer surface of the wire body 2 to positionally fix the tubular member relative to the wire body.

For example, the melted portions 77 can be formed by emitting energy such as a laser from the outer peripheral side to the tubular member 7 and by melting the tubular member 7 to be thermally deformed. In addition, the tapered portion 76 can be simultaneously formed with the respective melted portion 77 formed by emitting the aforementioned laser.

Figure 3A:
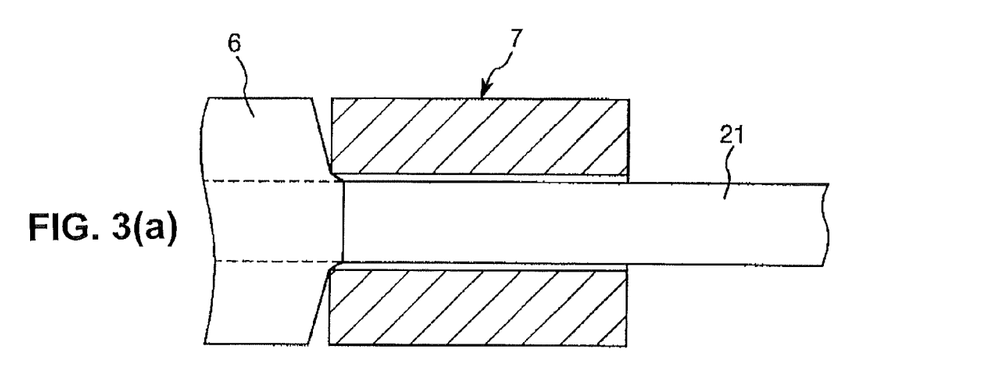
FIGS. 3(a)-3(c) are cross-sectional views illustrating an example of a manufacturing method of the tubular member illustrated in FIG. 2.

Specifically, for example, as illustrated in FIG. 3(a), the first wire 21 which is not welded to the second wire 22 and in which the distal side resin layer 6 is formed, and the tubular member 7 possessing the outer diameter which is constant in the longitudinal direction, are first prepared. Then, the tubular member 7 is inserted from the proximal side of the first wire 21 and is moved toward the resin coating layer to cause the tubular member 7 to abut on the proximal portion of the resin coating layer 6. In this state, the tubular member 7 is slidable with respect to the first wire 21.

Figure 3B:
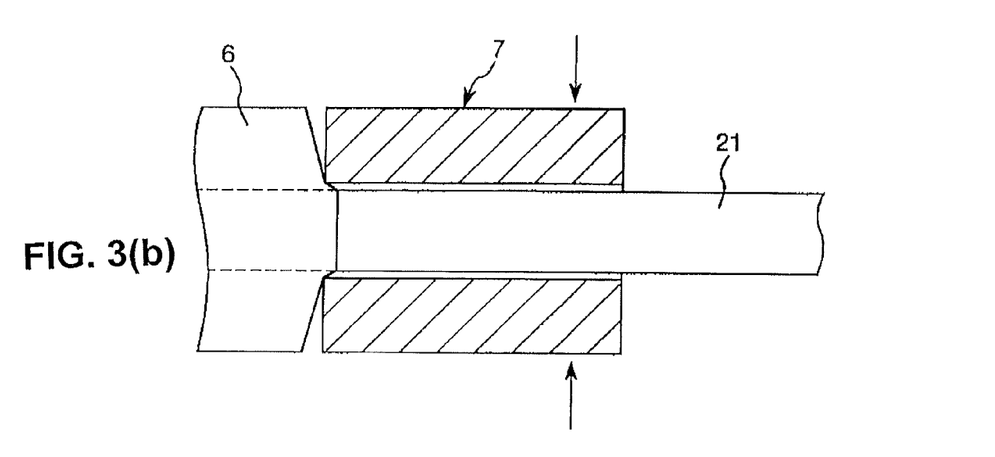
Figure 3C:
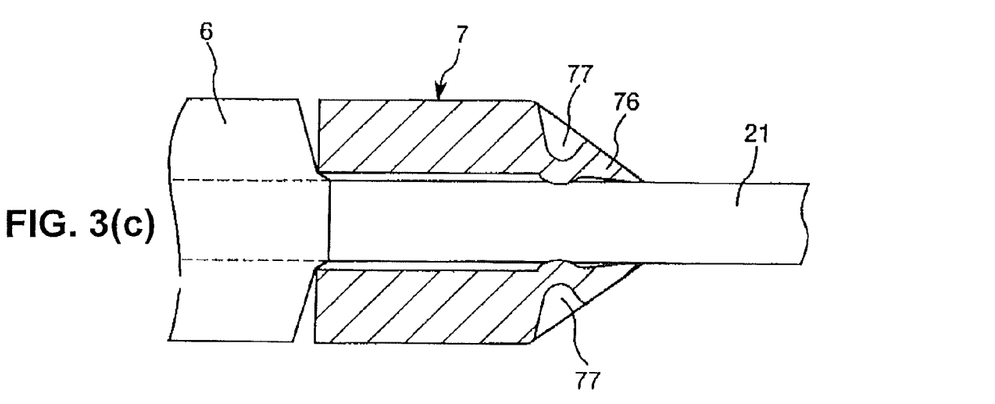

Subsequently, as illustrated in FIG. 3(b), multiple locations in the proximal portion of the tubular member 7 are irradiated with the laser, at portions indicated by arrows, in a spot shape (island shape). The multiple locations of the tubular member 7 that are irradiated with the laser are circumferentially spaced apart around the outer periphery of the tubular member 7.

Then, the laser irradiated portion is melted to be thermally and concavely deformed to the wire body 2. The laser irradiation of the spot-shaped regions causes the material forming the tubular member 7 to melt and form the inwardly directly protrusions. The laser irradiation thus produces the melted portions that protrude inwardly toward the wire body 2. The melted portions 77 formed by the deformation (laser irradiation) abut on (is brought into press contact with) the wire body 2 with a pressure to some extent. Accordingly, the wire body 2 is in a state of being caulked with the proximal portion of the tubular member 7, thereby fixing the tubular member 7 to the wire body 2. Moreover, as illustrated in FIG. 3(c), the front and the rear of the melted portions 77 are ground using a precision grinder while leaving concave portions, thereby forming the tapered portion 76. During a forming process of the melted portions 77, for example, burrs and the like are generated from the surroundings of the melted portions 77 as the melted portions 77 are formed. However, it is possible to form the tapered portion 76 while eliminating the burrs and the like.

Using the melted portions 77 formed in such a manner, the tubular member 7 is fixed to the wire body 2. Accordingly, it is possible to fix the tubular member 7 to the wire body 2 without using another member such as an adhesive agent or solder, for example. The tubular member 7 here is thus fixed in place relative to the wire body 2 without any adhesive, without any solder and without any other added part or material. Therefore, the guide wire 1 has a rather simple configuration and the guide wire 1 is relatively easily manufactured. In addition, for example, when fixing the tubular member 7 to the wire body 2 by using the aforementioned adhesive agent or solder, it is necessary to fill the gap S with the adhesive agent or the solder. Therefore, in order to fill the gap S with the adhesive agent or the solder, it is necessary to increase the thickness D of the gap S to some extent. This causes the tubular member 7 to be largely loosened from the wire body 2, thereby leading to a possibility of the degraded operability. In contrast, in the guide wire 1, the tubular member 7 is fixed to the wire body using the melted portions 77. Accordingly, the thickness D of the gap S can be thinner, and thus, it is possible to effectively prevent occurrence of the aforesaid problem.

In addition, since the melted portions 77 are fixed by melting, a site(s) corresponding to the melted portions 77 of the tubular member 7 has a lower rigidity than that of the other portions (site where melted portions 77 are not formed, for example, the distal portion). In the present embodiment, the melted portions 77 are formed in only the proximal portion of the tubular member 7, and thus, the rigidity of the proximal portion of the tubular member 7 is lower than the other portions of the tubular member (central portion of the tubular member and the distal portion of the tubular member). Accordingly, it is possible to change the rigidity (flexural rigidity, torsional rigidity) of the tubular member 7 toward the distal direction. Therefore, it is possible to improve the blood vessel tracking property of the guide wire 1, and it is also possible to prevent the guide wire 1 from being bent.

In other words, the melted portions 77 are irregularly formed along the longitudinal direction (axial direction) of the tubular member 7, and thus, the rigidity of the tubular member 7 can be changed in the longitudinal direction. The irregularly formed melted portions 77 include a non-symmetrical arrangement of the melted portions as well as melted portions that differ in size and area. Therefore, it is possible to exhibit the excellent operability or apply the desired operability.

Here, it is preferable not to weld the melted portions 77 to the wire body 2. In other words, it is preferable that the melted portions 77 and the wire body 2 not be integrated with each other by welding. This decreases thermal damage to the wire body 2, and thus, it is possible to configure the guide wire 1 to have excellent operability and the reliability.

In addition, it is preferable that the plurality of melted portions 77 be regularly (at equal spaced-apart intervals) formed along the circumferential direction of the tubular member 7. In addition, it is preferable that the shape and size of each melted portion 77 be substantially equal to each other. Accordingly, a bonding state of the tubular member 7 and the wire body 2 is regular (constant) along the circumferential direction of the tubular member 7, thereby improving the operability of the guide wire 1. Note that, in the plurality of melted portions 77, adjacent melted portions 77 may be separated from each other or may be in contact with each other.

It is preferable that the tubular member 7 be made of a material harder than the resin material configuring the resin coating layer 6, and it is preferable to use the metal material as the material thereof. As the metal material, for example, the stainless steel, the super-elastic alloy, the cobalt-based alloy, precious metals such as gold, platinum, tungsten and the like, or alloys containing these materials (for example, platinum-iridium alloy) can be exemplified. Particularly, it is preferable to employ the platinum-iridium alloy in a viewpoint of hardness and processing workability.

By disposing the tubular member 7, the distal of the catheter is prevented from coming into contact with the proximal 63 of the resin coating layer 6 while the distal crosses over the tubular member 7 to abut on the resin coating layer 6. As a result, even if the proximal 63 is slightly curled, the distal of the catheter is reliably prevented from being caught on the proximal 63.

In addition, in the guide wire 1, since the tubular member 7 and the wire body 2 are firmly fixed to each other by the melted portions 77 of the tubular member 7, even if the wire body 2 is curved near the tubular member 7, the tubular member 7 curves along the wire body 2. Therefore, since smooth bending can be realized without forming an unnecessary gap between the tubular member 7 and the wire body 2, it is possible to prevent a proximal side of the distal side coating layer 6 from being curled.

Next, referring to FIG. 4, a guide wire according to a second embodiment will be described. The description of the guide wire according to the second embodiment will primarily focus on differences between this embodiment and the first embodiment. Features in the second embodiment of the guide wire that are the same as in first embodiment are identified by common reference numerals and a detailed description of such features will not be repeated.

The guide wire according to the second embodiment is the same as the guide wire in the first embodiment except that the configuration of the tubular member is different.

Figure 4:
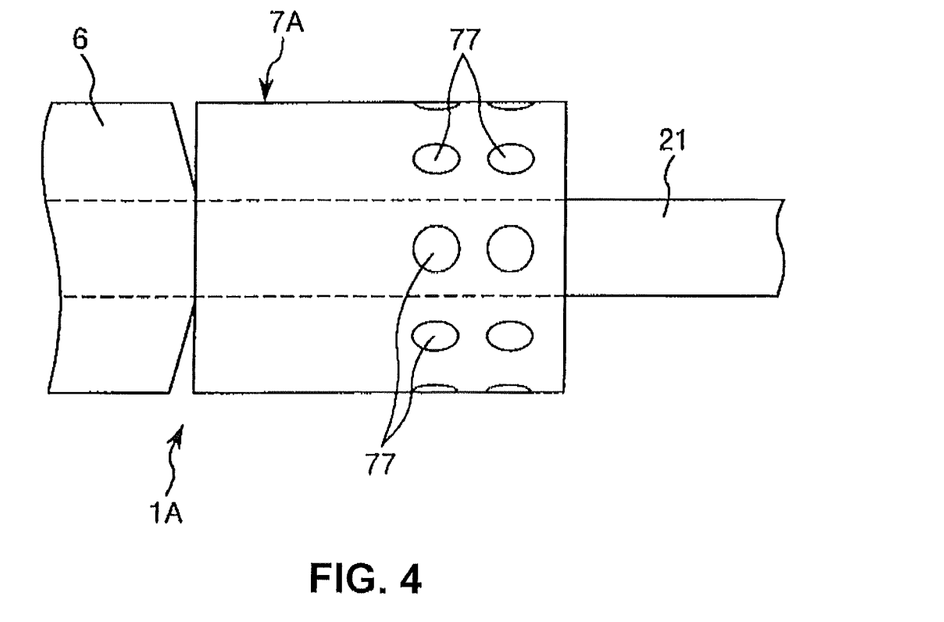
FIG. 4 is a plan view illustrating a tubular member included in a guide wire according to a second embodiment representing another example of the guide wire disclosed here.

As illustrated in FIG. 4, a tubular member 7A included in a guide wire 1A according to the present embodiment is substantially constant in its outer diameter throughout the entire region in the longitudinal direction. In other words, there is no tapered portion as in the aforementioned first embodiment. In addition, the plurality of melted portions 77 are formed on the proximal side of the tubular member 7. In contrast, the melted portion 77 is not formed on the distal side of the tubular member 7.

In this manner, the melted portions 77 are formed in the proximal portion of the tubular member 7, and thus, it is possible to exhibit the same effect as in the aforementioned first embodiment. In addition, since the melted portions 77 are not formed in the distal portion of the tubular member 7, it is possible to further separate heat which is generated when forming the melted portions 77 from the resin coating layer 6, and thus, it is possible to further reduce the heat transmitted to the resin coating layer 6. Therefore, it is possible to effectively prevent the resin coating layer 6 from melting.

According to the second embodiment, it is possible to exhibit the same effect as in the aforementioned first embodiment.

Next, referring to FIG. 5, a guide wire according to a third embodiment will be described. The description of the guide wire according to the third embodiment will primarily focus on differences between this embodiment and the first embodiment. Features in the third embodiment of the guide wire that are the same as in first embodiment are identified by common reference numerals and a detailed description of such features is not repeated.

The guide wire according to the third embodiment is the same as in the guide wire in the first embodiment except that the configuration of the tubular member is different.

Figure 5:
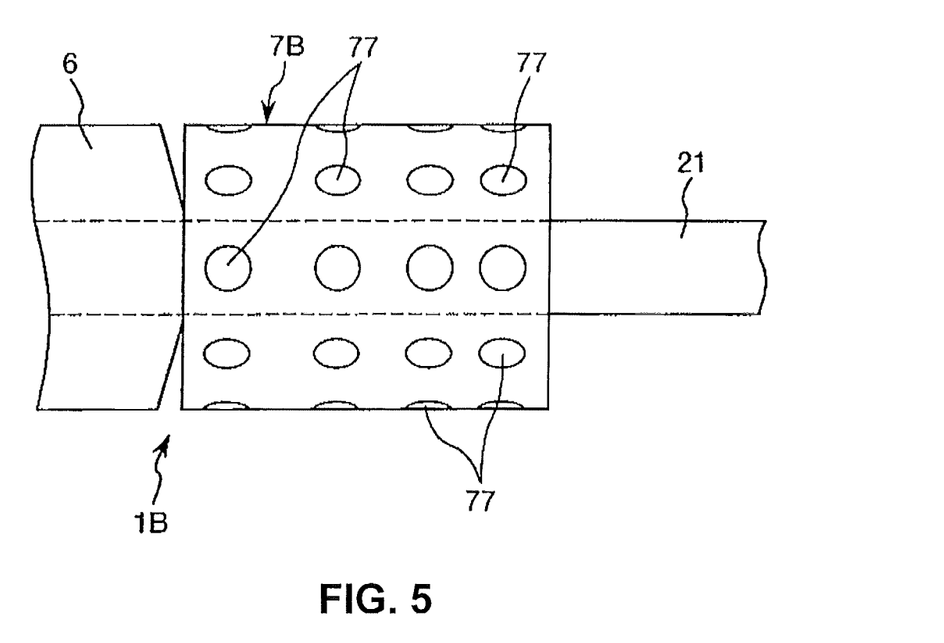
FIG. 5 is a plan view illustrating a tubular member included in a guide wire according to a third embodiment representing another example of the guide wire disclosed here.

As illustrated in FIG. 5, a tubular member 7B included in a guide wire 1B according to the present embodiment is substantially constant in its outer diameter throughout the entire region in the longitudinal direction. In other words, there is no tapered portion as in the aforementioned first embodiment.

In addition, the melted portions 77 are formed so as to cause an occupation rate with respect to an outer peripheral surface of the tubular member 7B to be lower on the distal side than the proximal side. That is, the area covered by the melted portions 77 per unit area in the distal side is less than the area covered by the melted portions 77 per unit area in the proximal side. Accordingly, it is possible to gradually increase the rigidity of the tubular member 7B toward the distal direction, and thus, it is possible to improve the blood vessel tracking property of the guide wire 1, and it is also possible to prevent the guide wire 1 from being bent.

Specifically, the plurality of melted portions 77 are configured to possess substantially same shape and size, and the tubular member 7B is formed in a state where its numbers included in a unit area on the outer peripheral surface (that is, density) gradually decrease from the proximal side toward the distal side. In addition, the melted portion 77 is formed throughout the entire region of the tubular member 7B in the longitudinal direction. Accordingly, with a relatively simple configuration, it is possible to gradually increase the rigidity of the tubular member 7B toward the distal direction.

Particularly, in the present embodiment, the melted portions 77 are formed in the proximal portion of the tubular member 7B as well as in the distal portion. The melted portions 77 are respectively formed in the proximal portion and the distal portion of the tubular member 7B, and the rigidity of each of the proximal portion and the distal portion is lowered, and thus, the proximal portion and the distal portion of the tubular member 7 are more easily deformed compared to a case where the melted portions 77 are not formed. Therefore, it is possible to enhance the tracking property with respect to the deformation of the wire body 2.

According to the third embodiment, it is possible to exhibit the same effect as in the aforementioned first embodiment.

Next, referring to FIG. 6, a guide wire according to a fourth embodiment will be described. The description of the guide wire according to the fourth embodiment will primarily focus on differences between this embodiment and the first embodiment. Features in the fourth embodiment of the guide wire that are the same as in first embodiment are identified by common reference numerals and a detailed description of such features will not be repeated.

The guide wire according to the fourth embodiment is the same as the guide wire in the first embodiment except that the configuration of the tubular member is different.

Figure 6:
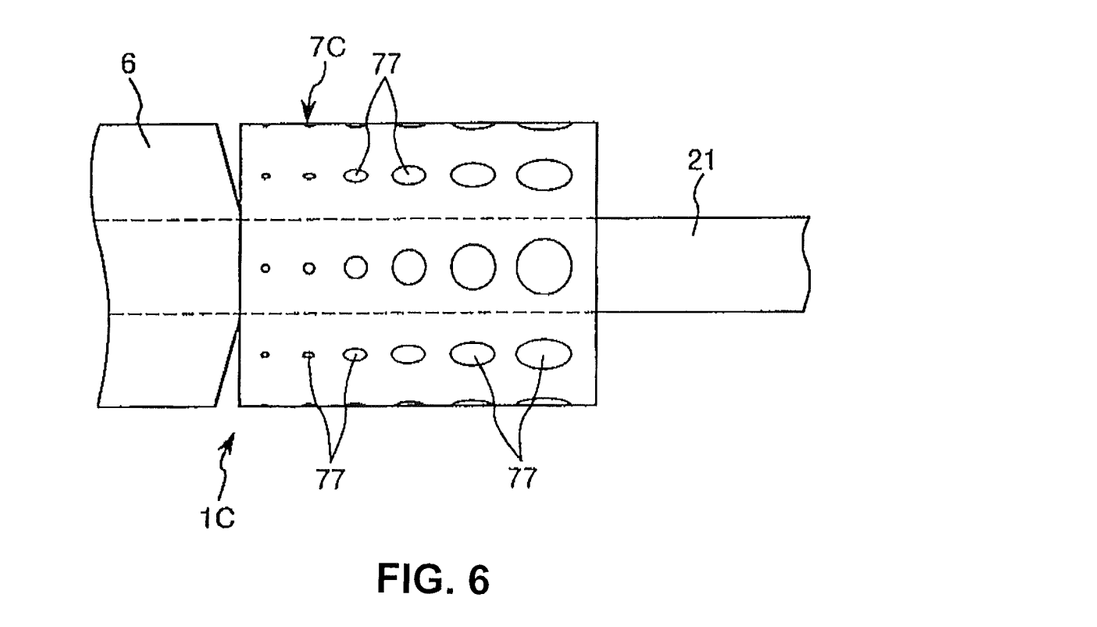
FIG. 6 is a plan view illustrating a tubular member included in a guide wire according to a fourth embodiment representing an additional example of the guide wire disclosed here.

As illustrated in FIG. 6, a tubular member 7C included in a guide wire 1C according to the present embodiment is substantially constant in its outer diameter throughout the entire region in the longitudinal direction. In other words, there is no tapered portion as in the aforementioned first embodiment.

In addition, the melted portions 77 are formed so as to cause the occupation rate with respect to an outer peripheral surface of the tubular member 7C to be lower on the distal side than the proximal side. That is, the area covered by the melted portions 77 per unit area in the distal side is less than the area covered by the melted portions 77 per unit area in the proximal side. Accordingly, it is possible to gradually increase the rigidity of the tubular member 7C toward the distal direction, and thus, it is possible to improve the blood vessel tracking property of the guide wire 1, and it is also possible to prevent the guide wire 1 from being bent.

Specifically, the plurality of melted portions 77 is formed in a state where the area covered by the melted portions 77 gradually decreases from the proximal side toward the distal side. In addition, the melted portions 77 are formed throughout the entire region of the tubular member 7C in the longitudinal direction. Accordingly, with the simple configuration, it is possible to gradually increase the rigidity of the tubular member 7C toward the distal direction.

According to the fourth embodiment, it is possible to exhibit the same effect as in the aforementioned first embodiment.

Next, referring to FIG. 7, a guide wire according to a fifth embodiment will be described. The description of the guide wire according to the fifth embodiment will primarily focus on differences between this embodiment and the first embodiment. Features in the fifth embodiment of the guide wire that are the same as in first embodiment are identified by common reference numerals and a detailed description of such features will not be repeated.

The guide wire according to the fifth embodiment is the same as the guide wire according to the first embodiment except that the configuration of the tubular member is different.

Figure 7:
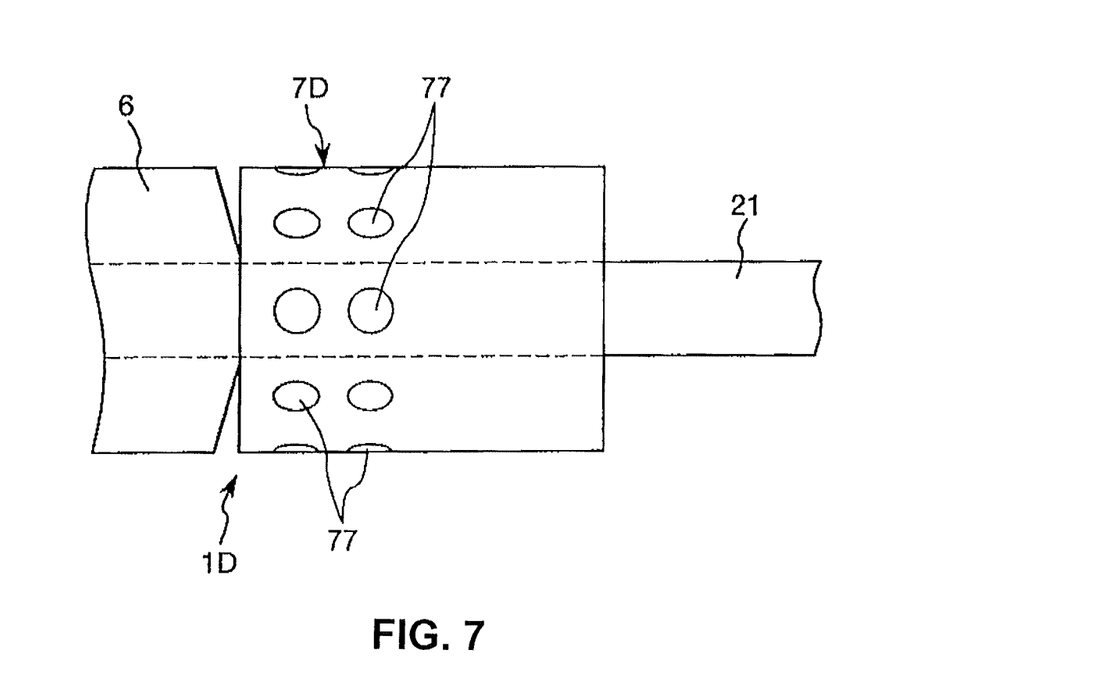
FIG. 7 is a plan view illustrating a tubular member included in a guide wire according to a fifth embodiment representing a further example of the guide wire disclosed here.

As illustrated in FIG. 7, a tubular member 7D included in a guide wire 1D according to the present embodiment is substantially constant in its outer diameter throughout the entire region in the longitudinal direction. In addition, the plurality of melted portions 77 is formed on the distal side of the tubular member 7, and the melted portions 77 are not formed on the proximal side of the tubular member 7.

In this manner, the melted portions 77 are formed at only the distal portion of the tubular member 7, and thus, it is possible to cause the rigidity of the distal portion of the tubular member 7D to be lower than the rigidity of the proximal portion. Therefore, the blood vessel tracking property of the guide wire 1 is improved.

According to the fifth embodiment, it is possible to exhibit the same effect as in the aforementioned first embodiment.

The description above describes the guide wire according to illustrated embodiments representing examples of the guide wire disclosed here. However, the present invention is not limited in this regard, and portions of the guide wire can be replaced with a differently configured portion which is able to exhibit a similar function. In addition, an arbitrarily configured material may be added to the guide wire.

In addition, in the aforementioned embodiments, a case where two wires are bonded to form the wire body is described. However, the wire body may be configured with one wire.

In addition, in the aforementioned embodiments, a case where the tubular member has a circular pipe shape is described. However, for example, the tubular member may have a shape where slits allowing the inside and the outside of the tubular member to communicate with each other throughout the entire region in the longitudinal direction, that is, a shape of a transverse section, to be in a C-shape.

A guide wire disclosed here includes an elongated wire body having flexibility; a distal side coating layer that covers a distal portion of the wire body and is configured of a resin material; and a tubular member that is positioned in the wire body and of which a distal portion is positioned in the vicinity of a proximal portion of the distal side coating layer. A plurality of melted portions which are concavely deformed to the wire body side by melting are formed in the tubular member. The tubular member is fixed to the wire body by bringing the melted portions into press-contact with the wire body. For this reason, since the tubular member and the wire body are firmly fixed to each other by the melted portions of the tubular member, even if the wire body is curved near the tubular member, the tubular member curves along the wire body. Therefore, since smooth bending can be realized without forming an unnecessary gap between the tubular member and the wire body, it is possible to prevent a proximal side of the distal side coating layer from being curled.

The detailed description above describes a guide wire disclosed by way of example. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A guide wire comprising:
   a flexible elongated wire body;
   a distal side coating layer covering a distal portion of the wire body and comprised of a resin material;
   a tubular member mounted on the wire body and possessing a distal portion positioned in a vicinity of a proximal portion of the distal side coating layer;
   the tubular member including a plurality of melted portions concavely deformed toward the wire body by melting; and
   the tubular member being fixed to the wire body by virtue of the melted portions being in press-contact with the wire body.

2. The guide wire according to claim 1, wherein the plurality of melted portions is irregularly formed along an axial direction of the tubular member.

3. The guide wire according to claim 1, wherein a portion of the tubular member at which the melted portions are located possesses a rigidity lower than the rigidity of other portions of the tubular member at which the melted portions are not located.

4. The guide wire according to claim 1, wherein the melted portions are located in a proximal portion of the tubular member.

5. The guide wire according to claim 4, wherein the tubular member has a tapered portion at which an outer diameter of the tubular member tapers toward a proximal side and the melted portions are located in the tapered portion.

6. The guide wire according to claim 1, wherein a density of melted portions per unit area in a proximal portion of the tubular member differs relative to the density of melted portions per unit area in the distal portion of the tubular member.

7. A guide wire comprising:
   a flexible elongated wire body possessing a distal end portion and a proximal end portion, the wire body also possessing an outer surface;
   a resin coating layer covering the distal end portion of the wire body, the resin coating layer possessing a proximal end;
   a tubular member mounted on the wire body so that the wire body passes though the tubular member while the tubular member encircles the wire body, the tubular member possessing a distal end in direct contact with the proximal end of the resin coating layer, the tubular member also possessing an outer surface and an inner surface, at least a proximal end portion of the tubular member encircling a portion of the wire body that is devoid of the resin coating layer;
   the tubular member including a plurality of circumferentially spaced apart melted portions at each of which the outer surface of the tubular member is concavely recessed and the inner surface of the tubular member projects as a protrusion in direct contact with the outer surface of the wire body to positionally fix the tubular member relative to the wire body; and
   the inner surface of the tubular member at places other than the protrusions is spaced from the outer surface of the wire body.

8. The guide wire according to claim 7, wherein the melted portions are non-symmetrically arranged along an axial direction of the tubular member.

9. The guide wire according to claim 7, wherein a portion of the tubular member at which the melted portions are located possesses a rigidity lower than the rigidity of other portions of the tubular member at which the melted portions are not located.

10. The guide wire according to claim 7, wherein the melted portions are located only in the proximal portion of the tubular member.

11. The guide wire according to claim 10, wherein the tubular member includes a tapered portion at which an outer diameter of the tubular member tapers in a narrowing manner in a direction away from the resin coating layer, and the melted portions are located in the tapered portion of the tubular member.

12. The guide wire according to claim 7, wherein the tubular member includes a tapered portion at which an outer diameter of the tubular member tapers in a narrowing manner in a direction away from the resin coating layer, and the melted portions are located in the tapered portion of the tubular member.

13. The guide wire according to claim 7, wherein the tubular member includes a tapered portion at which an outer diameter of the tubular member tapers in a narrowing manner in a direction away from the resin coating layer, and the melted portions are located only in the tapered portion of the tubular member.

14. The guide wire according to claim 7, wherein the melted portions are located in a proximal portion of the tubular member and also in a distal portion of the tubular member, an area covered by the melted portions per unit area in the distal portion of the tubular member being less than the area covered by the melted portions per unit area in the proximal portion.

15. The guide wire according to claim 7, wherein the melted portions are located in a proximal portion of the tubular member and also in a distal portion of the tubular member, a density of the melted portions gradually decreasing from the proximal portion of the tubular member to the distal portion of the tubular member.

16. A method of manufacturing a guide wire comprising:
positioning a tubular member in surrounding relation to an elongated wire, the wire including a distal portion covered by a resin coating layer, the resin coating layer possessing a proximal end, the tubular member possessing an outer surface and an inner surface, the tubular member also possessing a distal end portion;
the tubular member being positioned in surrounding relation to the elongated wire such that the tubular member directly contacts the proximal end of the resin coating layer; and
laser irradiating the tubular member at a plurality of spaced apart locations to melt material forming the tubular member and produce a plurality of spaced apart melted portions at each of which the outer surface of the tubular member is concavely recessed and the inner surface of the tubular member projects as a protrusion in direct contact with the outer surface of the wire body to positionally fix the tubular member relative to the wire body.

17. The method according to claim 16, wherein the tubular member positioned in surrounding relation to the elongated wire is a cylindrical tubular member, and further comprising tapering the distal end portion of the tubular member so that an outer diameter of the distal end portion of the tubular member gradually decreases in a proximal direction, the tapering occurring after the laser irradiating.

18. The method according to claim 16, wherein the tubular member positioned in surrounding relation to the elongated wire is a cylindrical tubular member, and further comprising tapering the distal end portion of the tubular member so that an outer diameter of the distal end portion of the tubular member gradually decreases in a proximal direction, the plurality of spaced apart locations that are laser irradiated being located in the distal end portion of the tubular member that is tapered.

* * * * *